United States Patent
Schmitz

[11] Patent Number: 5,797,896
[45] Date of Patent: Aug. 25, 1998

[54] DISPOSABLE ABSORBENT ARTICLE HAVING A LANDING MEMBER FOR ENGAGING WITH A HOOK-TYPE FASTENING MEMBER

[75] Inventor: Christoph Johann Schmitz, Euskirchen-Stotzheim, Germany

[73] Assignee: The Procter & Gamble Company, Cincinnati, Ohio

[21] Appl. No.: 860,125

[22] PCT Filed: Dec. 13, 1995

[86] PCT No.: PCT/US95/16676

§ 371 Date: Jun. 30, 1997

§ 102(e) Date: Jun. 30, 1997

[87] PCT Pub. No.: WO96/20677

PCT Pub. Date: Jul. 11, 1996

[30] Foreign Application Priority Data

Dec. 29, 1994 [EP] European Pat. Off. .............. 94120876

[51] Int. Cl.[6] ...................................................... A61F 13/15
[52] U.S. Cl. ............................................ 604/391; 604/389
[58] Field of Search ............................... 604/358, 370, 604/385.1, 385.2, 386, 387, 389, 390, 391

[56] References Cited

U.S. PATENT DOCUMENTS

| | | | |
|---|---|---|---|
| 3,335,721 | 8/1967 | Gastwirth | 604/391 |
| 3,359,980 | 12/1967 | Rosenblatt | 604/391 |
| 4,014,340 | 3/1977 | Cheslow | 128/287 |
| 4,585,450 | 4/1986 | Rosch et al. | 604/390 |
| 4,869,724 | 9/1989 | Scripps | 604/389 |
| 5,057,097 | 10/1991 | Gesp | 604/389 |
| 5,108,385 | 4/1992 | Snyder | 604/391 |
| 5,176,670 | 1/1993 | Roessler et al. | 604/391 |

*Primary Examiner*—Mary Beth Jones
*Assistant Examiner*—Francis K. Cuddihy
*Attorney, Agent, or Firm*—David M. Weirich; Steven W. Miller; Jacobus C. Rasser

[57] ABSTRACT

A mechanical fastening system for an absorbent article including a landing member comprising a loop-type material wherein the loop-type material underlies the backsheet. The absorbent article includes at least one cut-out section in the backsheet through which the loop-type material is exposed. The landing member may be a part of the fastening system for attaching the article on a wearer or may be a part of a disposal system for maintaining the diaper in a rolled-up disposal configuration.

13 Claims, 8 Drawing Sheets

DISPOSABLE ABSORBENT ARTICLE HAVING A LANDING MEMBER FOR ENGAGING WITH A HOOK-TYPE FASTENING MEMBER

FIELD OF THE INVENTION

This application is a 371 of PCT/US95/16676, filed Dec. 13, 1995.

The invention relates to disposable absorbent articles comprising a mechanical fastening system.

Such disposable absorbent articles are known from EP-A-0 321 234.

Known mechanical fastening systems for use in disposable absorbent articles comprise tape tabs in the back waist region comprising hook-type elements which mechanically engage with a landing member located in the front waist region. The landing member is a loop-type material which entangles with the hooks of the tape tabs to form a closure having resistance against peel forces and shear forces.

The known absorbent articles may comprise a landing member which is positioned in a region of the backsheet that is suitable to engage the hook-type tape tabs when the article is placer in a rolled-up disposal configuration.

The loop-type materials used for the landing members of the known mechanical fastening systems are relatively expensive materials.

Furthermore, the known loop-type materials are attached to the garment-facing side of the backsheet and form an extra layer that increases the bulk of the absorbent articles upon compression-packaging of these articles in a compressed array.

Finally, the addition of patches of loop-type material to the backsheet, adds to the complexity of the production process for making an absorbent article.

It is therefore an object of the present invention to provide an absorbent article having a mechanical closing system which is of simple construction and which is cost-effective.

It is another object of the invention to provide an absorbent article comprising a mechanical closing system which is of low bulk when packed in a compressed array.

It is again a further object of the present invention to provide an absorbent article having a mechanical closing system and comprising a simplified and effective disposal means for maintaining the article in a disposal configuration.

SUMMARY OF THE INVENTION

An absorbent article according to the invention comprises a garment-facing backsheet having two longitudinal sides, a front transverse edge, and a back transverse edge. The article has a mechanical closing system comprising at least two hook-type fastening members located in the region of the back transverse edge and extentending transversely beyond each longitudinal side. A landing member is located in the region of the front transverse edge or in another region of the backsheet for mechanically engaging with the hook-type fastening member. An inner layer covers the backsheet on the user-facing side thereof at least in the region of the landing member. The landing member comprises a cut-out section extending through the backsheet and exposing the underlying inner layer which is adapted to mechanically engage with the hook-type fastening members.

By cutting an aperture through the backsheet material, the inner layer below the backsheet is exposed through the aperture. The inner layer, which for instance comprises a fibrous non-woven layer, may be the topsheet which covers the absorbent core or may be a layer located between the topsheet and the backsheet. Alternatively, the inner layer may be a layer which is located below the absorbent core or may be a high wet-strength tissue which envelopes the core. By selecting the hook-type fastening members to match the non-woven material that is regularly employed as an inner layer, the hooks can mechanically engage with these layers to fasten the absorbent article around a wearer, or to maintain the absorbent article in a disposal configuration.

For fibrous inner layers having relatively little surface irregularities, relatively small and sharply pointed hooks will be required for the hook -type material of the fastening members to be able to engage with such a layer. For non-woven sheets or tissues which comprise a relatively large number of protruding loops at their surface, the hooks of the hook-type material may be of larger size and may be relatively flexible to obtain mechanical attachment to such sheets or tissues. Alternatively, the surface texture of the inner layers can be selected to match a given type of hook-fastening material to achieve proper fastening.

By using the nonwoven materials or other fibrous sheet materials which are usually employed on the user-facing side of the backsheet as a landing member, no additional loop-type material needs be employed as a landing member. The cutting of an apeture in the backsheet forms a process simplification compared to the step of adhesively connecting a separate loop-fastening material to the garment-facing side of the backsheet.

Furthermore, the landing member according to the invention does not result in an increase in bulk of the backsheet, such that the size of a compression-packed array of absorbent articles remains unaltered.

The cut-out section of the backsheet may form a fastening member to affix the article on a wearer. The fastening member may be formed by a single strip, extending parallel and adjacent the front waist edge of the backsheet, or may be formed by a number of individual cut-out sections to accommodate wearers of different sizes. The inner layer which is exposed by the cut-out section in the backsheet may be formed by the topsheet or may comprise any other layer located on the user-facing side of the backsheet. For instance, a layer of liquid-impervious material may be placed between the topsheet and the backsheet to overlie the edge of the core along the front waist edge as a barrier against leakage and which is exposed in the region of the cut-out section.

Alternatively, an elastic waist laminate may be comprised between topsheet and backsheet along the front waist edge. The elastic laminate may comprise a fibrous layer which projects through the cut-out sections. The elastic laminate may also be located on the user-facing side of the topsheet, the cut-out sections extending through both the topsheet and the backsheet. The use of the elastic laminate as a landing member has as an advantage that the material of the landing member is contracted to form gathers, which provide improved attachment with the hook material of the hook-type fastening members.

The backsheet may be comprised of a non-woven material, a thermoplastic film or a laminate, e.g. of a non-w oven material and a film. The backsheet may be formed of an elastic material. There may be additional layers located between the topsheet and the backsheet, the cut-out sections of the landing member extending through these additional layers.

The cut-out sections are preferably located outboard from the perimeter of the absorbent core to avoid leakage of body exudates from the core through the cutout sections. Alternatively, the cut-out sections can be located below the absorbent core, in particular when the cut-out regions are part of a disposal member for keeping the article in a rolled-up, or folded-over disposal configuration. In case the core comprises a fibrous absorbent material, such as fluff pulp, it is preferred that a loop-type web material is located between the core and the backsheet as the hook-type material cannot be properly fastened onto a fluff pulp core.

The shape of the cut-out sections can serve as a fit guide which helps positioning the absorbent article correctly on a user and which assures symmetrical attachment of the fastening members. The shape of the cut-out sections may for instance be chevron-type cut-out sections which are especially useful in combination with a low-cut front transverse edge.

In another embodiment of an absorbent article according to the invention, the cutout sections are covered by a cover member. This c over member may be an adhesive tape which is removed from the cut-out section when the diaper is put on a wearer. The cut-out sections which are not used for fastening, may remain covered by the cover member such that leakage cannot occur through these cut-out sections.

In one embodiment, the cover member of the landing member is on one side permanently attached to the backsheet, and comprises a hook-type material. The hook-type material of the cover member is engaged through the apertures of the cut-out sections with the underlying loop material. When the diaper is put on a wearer, the cover member is lifted, and the fastening members of the back waist section are connected to the exposed loop material of the cut-out sections. The back surface of the fastening members of the back waist section in this embodiment preferably comprises a loop-type material. The cover members can, after attaching the fastening members, be closed to engage with the loops on the back surface of the fastening members. In this manner a closure of improved shear strength is achieved.

In again an alternative embodiment, the cover member is formed by backsheet material. In such an embodiment, the backsheet material is not removed from the cut-out sections, but comprises a line of weakening which defines the cut out sections, and along which the backsheet material can manually be torn and removed to uncover the cut-out sections.

In a further embodiment, the cut-out section does not form a closure member but provides a disposal member. The disposal member is located inboard from the front transverse edge of the backsheet and is preferably located in closer proximity to the back waist region of the backsheet than the landing member of the closure member. In case the cut-out section forms a disposal member, the landing member of the closure system may comprise either similar cut-out sections or may comprise separate patches of loop-type material such as Velcro®-type material which are attached to the garment-facing side of the backsheet.

BRIEF DESCRIPTION OF THE DRAWINGS

The invention will be described in detail with reference to the accompanying drawings. In the drawings:

FIGS. 3–5a, and 5b show cross-sectional views of the absorbent article of FIG. 1 along a line of cross-section I—I running through the front waist region, substantially parallel to the front transverse edge, FIG. 15 shows a cross-sectional view along the line XV—XV of FIG. 14, and FIGS. 16 and 17 respectively show a side elevational view of an absorbent article comprising a cut-out section forming a disposal member, in the disposal configuration and the position of the hook-type fastening members in the disposal configuration.

DETAILED DESCRIPTION OF THE INVENTION

Mechanical closing systems of the present invention are useful and beneficial when applied to disposable absorbent articles. As used herein, the term "disposable absorbent article" refers to articles which absorb and contain body exudates and, more specifically, refers to articles which are placed against or in proximity to the body of the wearer to absorb and contain the various exudates discharged from the body and which are intended to be discarded after a single use (i.e., they are not intended to be laundered or otherwise restored or reused). A preferred embodiment of the disposable absorbent article of the present invention is a diaper 20. As used herein, the term "diaper" refers to a garment generally worn by infants or incontinent persons that is drawn up between the legs and fastened about the waist of the wearer. Examples of the kinds of diapers to which the present invention is very readily adapted are shown in the above-referenced U.S. Pat. Re. 26,151 issued to Duncan et al. and in U.S. Pat. No. 3,860,003 entitled "Contractable Side Portions for Disposable Diaper" which issued to Kenneth B. Buell on Jan. 14, 1975.

It will be apparent form the following description that the mechanical closing system illustrated and described herein may be applied to the body portion of such diapers. On the other hand, it will be understood that the invention is not limited to any specific diaper structure or configuration. As used herein, the term "closing-system" refers to a combination of hook-type fasteners and a loop-type landing member and comprises a fastening system for attaching the article on a wearer and a disposal system for keeping the article in a disposal configuration.

Figure 1:
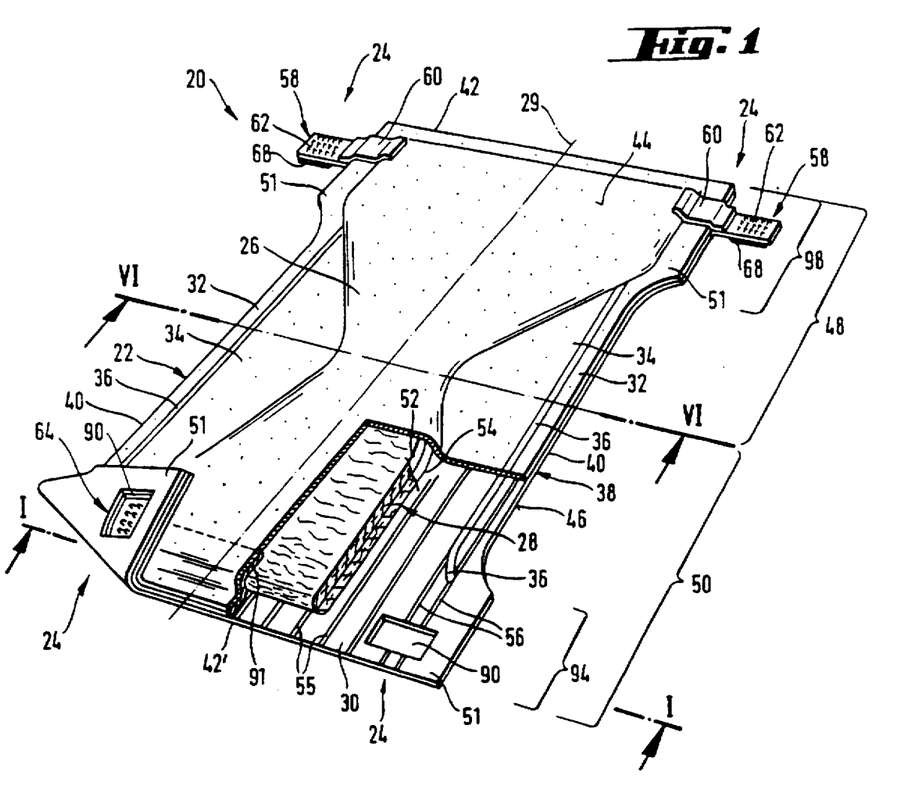
FIG. 1 shows a partially cut-away perspective view of a disposable diaper comprising a landing member according to the invention.

Referring to the drawings, it will be noted that FIG. 1 is a partially cut-away perspective view of the diaper 20 of the present invention prior to its being placed on the diaper wearer by the diaper user. As can be seen in FIG. 1, a preferred diaper 20 comprises a body portion 22 and a fastening system 24. A preferred body portion 22 comprises a liquid pervious topsheet 26, an absorbent core 28, a liquid impervious backsheet 30, and elastically contractible leg cuffs 32 comprising a side flap 34 and one or more elastic members 36. While the topsheet 26, the absorbent core 28, the backsheet 30, the side flaps 34, and the elastic members 36 may be assembled in a variety of well-known configurations, a preferred disposable diaper configuration is shown and described generally in the above-referenced U.S. Pat. No. 3,860,003 which issued to Kenneth B. Buell on Jan. 14, 1975.

FIG. 1 shows a preferred embodiment of the body portion 22 in which the topsheet 26 and the backsheet 30 are coextensive and have length and width dimensions generally larger than those of the absorbent core 28. The topsheet 26 is superposed on the backsheet 30 thereby forming the periphery 38 of the body portion 22. The periphery 38 defines the outer perimeter or, in other words, the outer extend of the body portion 22. The periphery 38 comprises longitudinal sides 40 and end edges or transverse edges 42, 42'. The body portion 22 has userfacing side 44 and garment-facing 46. In general, the garment-facing side 46 of the diaper 20 extends from back transverse edge 42 to front transverse edge 42' of the diaper and from one longitudinal side 40 to the other longitudinal side 40 of the diaper and is the surface farthest from the wearer during use of the diaper 20. The garment-facing side of any layer comprised in the diaper 20 is the side of the layer farthest from the wearer during use. When a backsheet 30 is used, it typically forms the garment-facing side 46 of the body portion 22. The user-facing side 44 is that surface of the diaper opposite the garment-facing side 46 and in the embodiment shown is typically formed by the topsheet 26. In general, the userfacing side 44 of the diaper 20 is that surface coextensive with the garment-facing side 46 and which is for the greater part in contact with the wearer when the diaper 20 is worn. The user-facing side of any layer comprised in the diaper 20 is that side of the layer which is located closest to the wearer during use.

The diaper 20 has first and second end regions 48 and 50, respectively, extending from the back and front transverse edges 42, 42' of the diaper periphery 38 toward the transverse centerline of the diaper 20. Both the first end region 48 and the second end region 50 extend a distance of about one-half of the length of the diaper 20 such that the end regions comprise each half of the diaper 20.

Both the first end region 48 and the second end region 50 have panels 51. The panels 51 are those portions of the first end region 48 and the second end region 50 which overlap when the diaper 20 is fastened about the waist of the wearer. The extent to which the end regions overlap and thus the extent to which the panels 51 are formed will depend on the overall dimensions and shape of the diaper 20 and the size of the wearer.

The absorbent core 28 of the body portion 22 may be any means which is generally compressible, conformable, non-irritating to the wearer's skin, and capable of absorbing and retaining liquids and certain body exudates. The absorbent core 28 may be manufactured in a wide variety of sizes and shapes (e.g., rectangular, hourglass, asymmetric, etc.) and from a wide variety of liquid absorbent materials commonly used in diapers and other disposable absorbent articles, such as comminuted wood pulp which is generally referred to as the airfelt. Examples of other suitable absorbent materials include creped cellulose wadding, absorbent foams, absorbent sponges, superabsorbent polymers, absorbent gelling materials, or any equivalent materials or combination of materials. The total absorbent capacity of the absorbent core 28 should, however, be compatible with the design exudate loading in the intended use of the diaper 20. Further, the size and absorbent capacity of the absorbent core 28 may varied to accommodate wearers ranging from infants to adults.

While the absorbent core 28 may comprise a single layer of absorbent material such as the configuration described in U.S. Pat. No. 4,610,678 entitled "HighDensity Absorbent Structure" which issued to Paul T. Weisman and Steven A. Goldman on Sep. 9, 1986 a preferred embodiment of the absorbent core 28 is a dual-layered absorbent core in a preferred configuration such as is generally described in U.S. Pat. No. 4,673,402 entitled "Absorbent Article With Dual-Layered Cores" which issued to Paul T. Weisman, Dawn I. Houghton and Dale A. Gellert on Jun. 16, 1987, having an asymmetric-shaped upper layer 52 and a lower layer 54. The upper layer 52 preferably acts as a liquid acquisition/distribution layer comprised primarily of hydrophilic fiber material. The lower layer 54 acts as a liquid storage layer comprised of a mixture of hydrophilic fiber material and particles of an absorbent gelling material (hydrogel material).

Both the upper layer 52 and the lower layer 54 preferably comprise an absorbent layer encased in a tissue layer. It should be understood, however, that the size, shape, configuration, and total absorbent capacity of the upper layer 52 or the lower layer 54 may be varied to accommodate wearer's ranging from infants through adults. Therefore, the dimensions, shape, and configuration of both the upper layer 52 and the lower layer 54 may be varied (e.g., the upper layer or the lower layer may have a varying caliper, a hydrophilic gradient, a rapid acquisition zone or may contain absorbent gelling material).

The absorbent core 28 is superposed on the backsheet 30 and is preferably associated thereto by a core attachment means 55 such as those well known in the art, for example, pressure-sensitive adhesives, hot melt adhesives or other adhesives; ultrasonic bonding; or heat/pressure sealing. The absorbent core 28 may be secured to the backsheet 30 by a uniform continuous layer of adhesive, a patterned layer of adhesive, or any array of separate lines or spots of adhesive. And adhesive which has been found to be satisfactory is preferably a hot-melt adhesive such as manufactured by Eastman Chemical Products Company of Kingsport, Tenn. and marketed under the tradename of Eastobond A-3 or by Century Adhesives, Inc., of Columbus, Oh. and marketed under the tradename Century 5227. The core attachment means 55 preferably comprise an open pattern network of filaments of adhesive as is shown in U.S. Pat. No. 4,573,986 entitled "Disposable Waste-Containment Garment" which issued to James A. Minetola and David R. Tucker on Mar. 4, 1986.

The backsheet 30 is impervious to liquids and is preferably manufactured from a thin plastic film, although other flexible liquid impervious materials may also be used. The backsheet 30 prevents the exudates absorbed and contained in the absorbent core 28 from soiling articles which contact the diaper 20 such as bedsheets and undergarments. Preferably, the backsheet 30 is a polyethylene film having a thickness of from 0.012 mm (0.5 mil) to 0.051 mm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 30 is preferably embossed and/or matte finished to provide a more clothlike appearance. Further, the backsheet 30 may permit vapors to escape from the absorbent core 28 while still preventing exudates from passing through the backsheet 30.

The size of the backsheet 30 is dictated by the size of the absorbent core 28 and the exact diaper design selected. In a preferred embodiment, the backsheet 30 has a modified hourglass shape extending beyond the absorbent core a minimum distance of at least 0.5 cm to 8 cm preferably 1.3 cm to 2.5 cm, around the entire diaper periphery 38.

The topsheet 26 of the body portion 22 of the present invention is compliant, soft feeling, and non-irritating to the wearer's skin. Further, the topsheet 26 is liquid pervious permitting liquids to readily penetrate through its thickness. A suitable topsheet 26 may be manufactured from a wide range of materials such as porous foams, reticulated foams, apertured films, natural fibers (e.g. wood or cotton fibers), synthetic fibers (e.g., polyester or polypropylene fibers) or from a combination of natural and synthetic fibers. Preferably, it is made of a hydrophobic material to isolate the wearer's skin from liquids retained in the absorbent core 28.

A particularly preferred topsheet 26 comprises staple length polypropylene fibers having a denier of about 1.5, such as Hercules Type 151 polypropylene fibers marketed by Hercules, Inc. of Wilmington, Delaware. As used herein, the term "staple length fibers" refer to those fibers, having a length of at least 15.9 mm (0.625 inches).

There are a number of manufacturing techniques which may be used to manufacture the topsheet 26. For example, the topsheet 26 may be woven, nonwoven, spunbonded, carded, hydroformed or the like. A preferred topsheet 26 is carded and thermally bonded by means well-known to those skilled in the fabric art. Preferably, the topsheet 26 has a basis weight from 15 to about 30 grams per square meter, a minimum dry tensile strength of at least 400 grams per centimeter in the machine direction and a wet tensile strength of at least 55 grams per centimeter in the cross-machine direction.

The topsheet 26 and the backsheet 30 are associated together in any suitable manner as is well known in the diaper manufacturing art. As used herein, the term "associated" encompasses configurations whereby the topsheet 26 is directly joined to the backsheet 30 by affixing the topsheet 26 directly to the backsheet 30, and configurations whereby the topsheet 26 is indirectly joined to the backsheet 30 by affixing the topsheet 26 to intermediate members which in turn are affixed to the backsheet 30. In a preferred embodiment, the topsheet 26 and the backsheet 30 are joined directly to each other in the diaper periphery 38 by a flap attachment means 56 such as an adhesive or any other attachment means as is known in the art. In general, the core attachment means 55 that affixes the absorbent core 28 to the backsheet 30 is the same means as the flap attachment means 56 that affixes the topsheet 26 to the backsheet 30. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

Elastically contractible leg cuffs 32 are disposed adjacent the periphery 38 of the body portion 22, preferably along each longitudinal edge 40, so that the leg cuffs 32 tend to draw and hold the diaper 20 against the legs of the wearer. While the leg cuffs 32 may comprise any of several means as are well known in the diaper art, a particularly preferred leg cuff construction comprises a side flap 34 and one or more elastic members 36, as is described in detail in the hereinbefore referenced U.S. Pat. No. 3,860,003. In addition, a method and apparatus suitable for manufacturing a disposable diaper having elastically contractible leg cuffs are described in U.S. Pat. No. 4,081,301 entitled "Method and Apparatus For Continuously Attaching Discrete, Stretched Elastic Strands to Predetermined Isolated Portions of Disposable Absorbent Articles" which issued to Kenneth B. Buell on Mar. 28, 1978.

In a preferred embodiment, the elastically contractible leg cuff 32 comprises a side flap 34 and an elastic member 36 comprising an elastic thread.

The diaper 20 is provided with a fastening system 24 for forming a side closure. Thus, the diaper 20 is fitted to the wearer and the first end region 48 and the second end region 50 are maintained in an overlapping configuration when the diaper 20 is worn.

In a preferred embodiment of the present invention as shown in FIG. 1, the fastening system 24 comprises a fastening member 58, preferably being formed by a tape tab 60 and a hook-type fastening element 62, disposed adjacent each longitudinal side 40 of the body portion 22 in the back waist region 98 of the first end region 48. A landing member 64, engageable with the hook-type fastening element 62, is disposed on the garment-facing surface 46 of the body portion 22 in the front waist region 94. Additional fastening/disposal means 68 may be positioned on the tape tab 60, for allowing the diaper 20 to be secured in a disposal configuration so as to provide convenient disposal of the diaper 20.

Each fastening member 58 is intended to provide a mechanical fastening means for engaging the landing member 64 so as to provide a secure side closure for the diaper 20.

The fastening member 58 comprises combination of a hook-type fastening element and adhesive attachment means positioned on the body portion 22 of the diaper 20. The hook-type fastening element 62 of each fastening member 58 is joined to the body portion and preferably covers an area 25 mm wide (i.e., generally perpendicular to longitudinal centerline) by 62.5 mm long (i.e., generally parallel to the longitudinal centerline) at the panels 51 of the body portion 22. An exemplary embodiment of a hook-type fastening member 62 is described in U.S. Pat. No. 4,699,622 entitled "Disposable Diaper Having an Improved Side Closure" issued to John W. Toussant and Margaret H. Hasse on Oct. 13, 1987.

Figure 2:
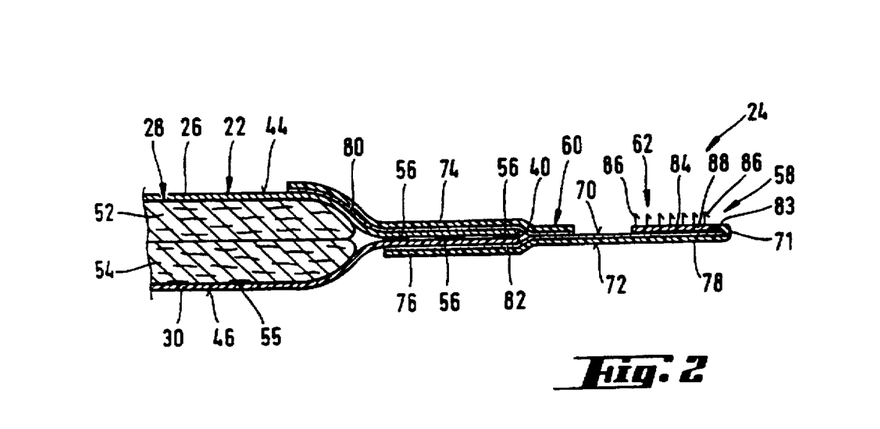
FIG. 2 shows a cross-sectional view through a hook-type fastening member of FIG. 1 along a line of cross-section extending parallel to the back transverse edge.

As shown in FIGS. 1 and 2, the fastening member 58 most preferably comprises a tape tab 60. Any of the well known configurations and constructions of a tape tab may be used. A preferred tape tab 60 is a Y-shaped tape tab as described in detail in GB-A-1458566. Alternatively preferred tape tabs are described in detail in co-pending European Patent Application No. 87300450.1.

A particularly preferred tape tab 60 is illustrated in FIG. 2 and has a fastening surface 70 and a backing surface 72. The fastening surface 70 is that surface of the tape tab 60 designed to engage the landing member 64 of the present invention. Thus, the fastening surface 70 of the tape tab 60 will generally correspond to the garment-facing side 44 of the body portion 22. The backing surface 72 is that surface opposite of the fastening surface 70 and generally corresponds to the outside surface 46 of the body portion 22. The backing surface 72 is thus generally exposed during wear of the diaper 20.

The preferred tape tab 60 illustrated in FIG. 2 is one which is anchored to both the user-facing side 44 and the garment-facing side 46 of the body portion 22 to create a manufacturer's end (i.e., that attachment of the tape tab 60 to the diaper 20 made during manufacture of the diaper 20). The tape tab 60 has another element which forms the user's end i.e., that joint made by the person in securing the diaper to the wearer). Thus, the preferred tape tab 60 of the present invention has at least three elements, a first fixed portion 74, a second fixed portion 76, and a connective portion 78. The first fixed portion 74 is that portion of the tape tab 60 which is attached to the user-facing side 44 of the body portion 22. The second fixed portion 76 is that portion of the tape tab 60 which is attached to the garmentfacing side 46 of the body portion 22. The first fixed portion 74 and the second fixed portion 76 thus form the manufacturer's end of the tape tab 60. The connective portion 78 is that portion of the tape tab 60 which is attached to another portion of the diaper 20, generally the landing member 64 by the user when securing the diaper 20 on the wearer. The connective portion 78 thus forms the user's end. Additionally, the outer surface of the second fixed portion 76 and the outer surface of the connective portion 78 form the backing surface 72 of the tape tab 60 while the inner surface of the first fixed portion 74 and the inner surface of the connective portion 78 form the fastening surface 70 of the tape tab 60.

The preferred Y-shaped tape tab 60 of the present invention can be constructed in several ways. The first fixed portion 74, the second fixed portion 76, and the connective portion 78 can each be separate tapes which meet and are joined adjacent the longitudinal edge 40 of the body portion 22 in an area of joinder. A more practical structure for the tape tab 60 is one in which the connective portion 78 and either the first fixed portion 74 or the second fixed portion 76 are a unitary strip of tape material. If the connective portion 78 is unitary with the second fixed portion 76 as shown in FIG. 2, then the first fixed portion 74 is a separate element which is attached to the combined connective portion and the second fixed portion adjacent to the longitudinal side 40 of the body portion 22. FIG. 2 also shows tab attachment means for securing the tape tab 60 to the body portion 22. These tab attachment means are any of those attachment means which provide an adequate bond, and preferably are any of the pressure-sensitive adhesives well-known to those of ordinary skill in the adhesive art. The outer surface of the first fixed portion 74 is affixed to the user-facing side 44 of the body portion 22 by a first tab attachment means 80. The inner surface of the second fixed portion 76 is affixed to the garment-facing side 46 of the body portion 22 by a second tab attachment means 82. The connective portion is provided with a first fastening element 62 joined to it preferably by the second tab attachment means 82 (alternatively, a third tab attachment means if the connective portion 78 is a separate element from the second fixed portion 76), although an adhesive attachment means may be placed on the first fastening element 62 separately and the combined material joined to the connective portion 78.

Preferred materials for the tape tabs 60 comprises a tape material such as tape code numbers XPF 14.43.0, Y-9376, or Y-9030 available from The Minnesota Mining and Manufacturing Company, St. Paul, Minn. The tape material in the embodiments are preferably a polyethylene film having a tab attachment means tailored to bond to the polyethylene positioned on the tape material. The tape tab attachment means may comprise any of those adhesives which provide an adequate bond with other portions of the diaper, and is preferably any of the pressure-sensitive adhesives well-known to those of ordinary skill in the art. Preferred tab attachment means is a pressure-sensitive adhesive such as code number XPF 1.42.34 available from The Minnesota Mining an Manufacturing Company, St. Paul, Minn.

As shown in FIG. 2, the tape tab 60 may also have a grip tab 83 at the distal edge 71 in the connective portion 78. The grip tab 83 may be formed by folding over a small margin of the distal edge 71 of the connective portion 78 and attaching it to itself. This forms an end on the connective portion 78 which is easier to grasp by the diaper user when the diaper 20 is to be fitted and attached to the wearer. The grip tab 83 is most beneficial when used when the connective portion 78 is superposed on the first fixed portion 74.

The hook-type fastening element 62 of the present invention comprises a hook fastening material 84. As used herein, the term "hook fastening material" is used to designate a material having engaging elements 86. It should also be understood that the use of the term "hook" should be non-limiting in the sense that the engaging elements 86 may comprise any shapes as are known in the art so long as they are adapted to engage a complementary second fastening element 66. As shown, the hook fastening material 84 preferably comprises a base 88 having a first surface and a second surface and a plurality of engaging elements 86 extending from the first surface of the base 88. Each of the engaging elements 86 are shown to comprise a stem supported at one end on the first surface of the base and an enlarged head positioned at the end of the stem opposite of the base.

The hook fastening material 84 of the present invention is intended to engage fibrous elements of fibrous material on the user-facing side 44 of the backsheet, which fibrous material may for instance be formed by the topsheet 26 or by a waist shield 91. Thus, the hook fastening material 84 may be manufactured from a wide range of materials. Suitable materials include nylon, polyester, polypropylene, or any combination of these materials. A suitable hook fastening material 84 comprises a number of shaped engaging elements 86 projecting from a woven backing such as the commercially available material designated "Scotchmate" brand No. FJ3402 available from Minnesota Mining and Manufacturing Company, St. Paul, Minn. Alternatively, the engaging elements may have any shape such as hooks, "T's" or any other shape as are well known in the art. A particularly preferred hook fastening material is described in C. Locke Scripps' co-pending U.S. patent application Ser. No. 07/007,841 entitled "Disposable Diaper Having An Improved Fastening Device" filed Jan. 26, 1987, in EP-A-0 382 024 and U.S. Pat. No. 5,325,569. Other suitable hook-type materials for use in the present invention are for instance extruded hooks available under the reference MC5 from the Minnesota Mining and Manufacturing Company, ST. Paul, Minn. or printed hooks available from the same company under references CS200 and MC6. Other suitable hook-type materials are available under reference 942 or 960E from Aplix, Inc., P.O. Box 7505, Charlotte, N.C. 28241.

In FIG. 1, the cut-out sections 90 are shown to extend through the backsheet 30. The cut-out section on the left-hand side exposes an inner layer 91 which forms a loop-type landing zone which can mechanically engage with the hook-type material of fastening members 58.

The inner layer 91 shown in FIG. 1 is part of a waist-shield layer that extends between the topsheet 26 and the backsheet 30 in the front waist region 94 to prevent leakage from the core 28. Layer 91 can also be fixed to topsheet 26, on the user-facing side 44 thereof. In this case, the cut-out sections 90 would extend through the topsheet 26.

As used herein, the term "loop-type" material is intended to mean any fibrous material which can mechanically engage with the hook-type material of the fastening members 58 to maintain the diaper 20 affixed around the waist of a wearer, or in a disposal configuration. A useful loop-type material has been described in U.S. pat. No. 5,326,612 (Goulait). Other suitable loop-type materials for use in the present invention may comprise woven materials such as brushed loops available from Texmaille S.A., Rue Pasteur, 02610 Moy de L'aisne, France; double knit loops available from Tissages de Quintenas S.A., Parc d'activités de marenton, B.P. 158-07104 Annonay, France; and Linerless loops available under reference LLL from the Minnesota Mining and Manufacturing Company.

Again other suitable loop-type materials are formed by non-woven materials.

In general, the materials of the hook-type fastening members 58 and the loop-type landing member 64 should be selected such that the peel force of a 30 mm wide patch of hook-type material is between 3 and 20N, preferably about 7–8N and the shear force of a patch of hook-type material of dimensions of 30×13 mm is between 10 and 100N, preferably about 50N.

The tests for measuring the peel forces and the shear forces exerted by the hook-type fastening members 58 on the loop type landing member 64 are described below.

I. 135°—Peelforce Test

This method describes the procedure for measuring the peel force, in grams, of the combined hook-type fastening member and loop-type landing member. The materials under test are mounted on a steel plate-sled assembly and are separated at a constant peel angle of 135°.

During the test the temperature is maintained at 73°±2° F. The relative humidity is controlled at 50±2%.

A patch of loop-type material measuring 2 in.×4 in. is placed on a 2 in.×8 in. ×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined towards the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted into an INSTRON test apparatus, Model 4201, which is set to have a cross-head speed of 12 in./minute and a Load Cell of 1 kg.

The steel plate is slidably mounted in a sled which is carried by the lower jaw of the INSTRON apparatus.

The leading edge of the tape tab 60 is placed in the upper jaw of the INSTRON apparatus .

The upper cross head is set in motion to pull the leading edge of the tape tab 60 off the loop-type landing member at an angle of 135° with respect to the loop-type landing member. The steel test plate on which the loop-type landing member is mounted, is moved in the sled simultaneously with the cross head relative to the lower jaw to maintain a constant angle of 135° during the full cycle of peeling off the tape tab.

The peak force, in grams, is recorded for at least four samples and is averaged.

II. 180° Shear Test

This method describes the procedure for measuring the shear force, in grams, of the combined hook-type fastening member and loop-type landing member. The materials under test are mounted on a steel plate and are separated at a constant peel-angle of 180° .

During the test the temperature is maintained at 73±2° F. The relative humidity is controlled at 50±2%.

A patch of loop-type material measuring 2 in.×5 in. is placed on a 2 in.×5 in. ×0.06 in. steel plate with a double-sided tape of the same dimensions as the patch of loop-type material.

A patch of hook-type material measuring 1 in.×0.75 in. is attached to a tape tab of similar kind as the tape tab 60 shown in FIG. 1, adjacent the area of the grip tab 83, further referred to in this test method as the leading edge of the tape tab 60. No actual grip tab needs be present at the leading edge of the tape tab 60 during testing. If the hooks of the hook-type material are angled with respect to the tape tab, the hooks are oriented to be inclined away from the leading edge.

The hook-type material is placed on the loop-type landing member. Subsequently, a rubber-coated steel roller of diameter of 3.25 in., a width of 1.75 in. and a weight of 4.5 lbs is rolled back and forth in the length direction of the tape tab 60 twice (a total of four passes).

The steel plate with the attached hook-type and loop-type materials is mounted horizontally into the lower jaw of an INSTRON test apparatus, Model 4201, which is set to have a cross-head speed of 12 in./minute, a Load Cell of 10.0 kg and a gage length of 2 in.

The leading edge of the tape tab 60 is placed in the upper jaw of the INSTRON apparatus .

The upper cross head is set in motion to pull the leading edge of the tape tab 60 off the loop-type landing member at an angle of 185° with respect to the loop-type landing member. When the maximum pull force has been reached, the crosshead is returned to the pre-set gage length.

The peak force, in grams, is recorded for at least four samples and is averaged.

Figure 3:
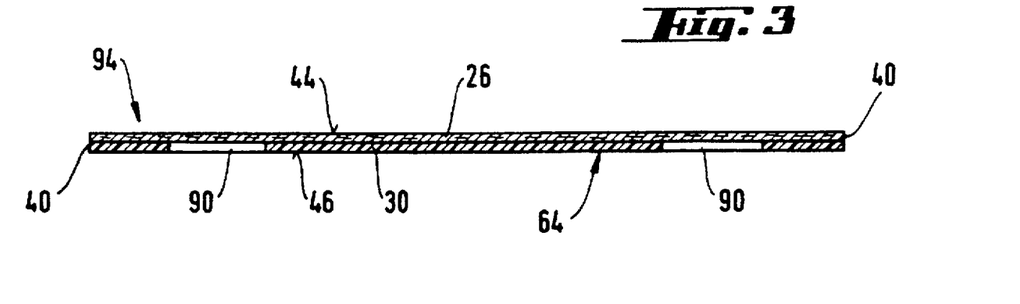

FIG. 3 shows a cross-sectional view of the landing member 64 along a line of crossection I—I in FIG. 1 located along the front transverse edge 42' in the front waist region 94. The cut-out section, or holes 90 through the backsheet 30 expose the topsheet 26 which forms the inner layer which can engage with the hooks of the fastening member 58.

Figure 4:
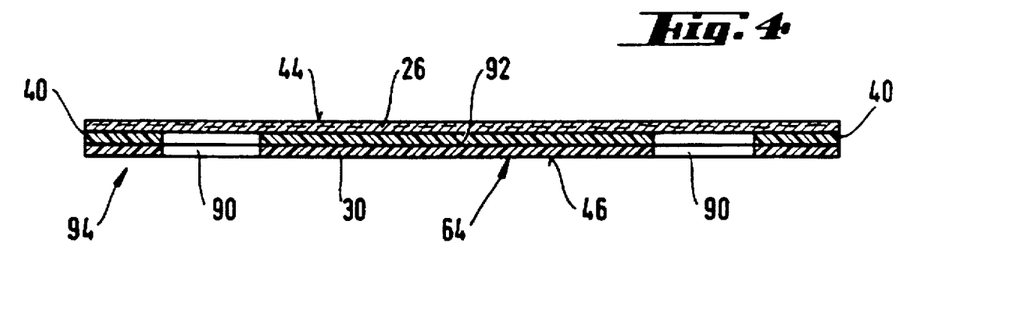

FIG. 4 shows a cross-sectional view of the landing member 64, located in the front waist region 94, wherein an additional layer 92 is comprised between the topsheet 26 and the backsheet 30. The additional layer 92 may for instance be a liquid-impervious thermoplastic layer, which extends between the topsheet 26 and the core 28 in the front waist region 94 as a waist shield, to prevent leakage from the transverse edges of the core. In case the additional layer 92 is unsuitable to engage the hooks of the fastening member 58, which is the case when the layer 92 is a plastic film, then the cuts 90 extend through this layer to expose the topsheet 26.

Alternatively the additional layer 92 and the backsheet 30 in FIG. 4 may be laminated, the backsheet 30 comprising a fibrous material that is unsuitable for providing sufficient mechanical attachment to the fastening members 58, the inner layer 92 being a thermoplastic film.

Figure 5A:
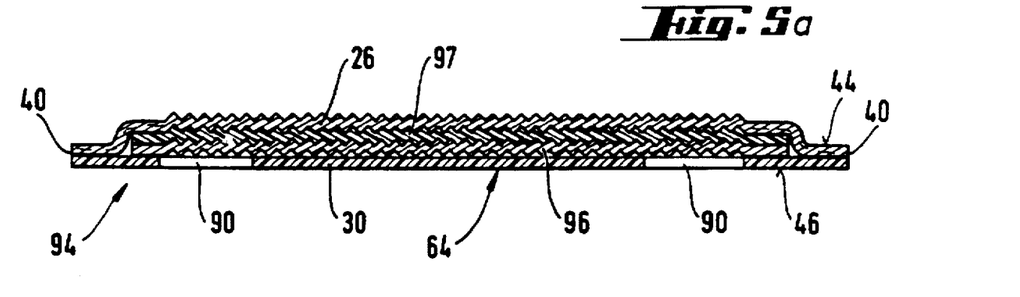

FIG. 5a depicts another embodiment of a cross-section of the front waist region 94 of a diaper 20, wherein an elastic laminate 96,97 is comprised along the front waist edge 42' between the topsheet 26 and the backsheet 30. The laminate comprises a nonwoven layer 96 and an elastomeric film 97 attached to the nonwoven layer 96. The elastic laminate contracts the front waist edge 42' in a number of gathers such that the fibers of the layer 96 project outwardly through the apertures 90. Hereby the fastening capacity of the hook-type fastening element 62 to the fibers of layer 96 is improved.

Figure 5B:
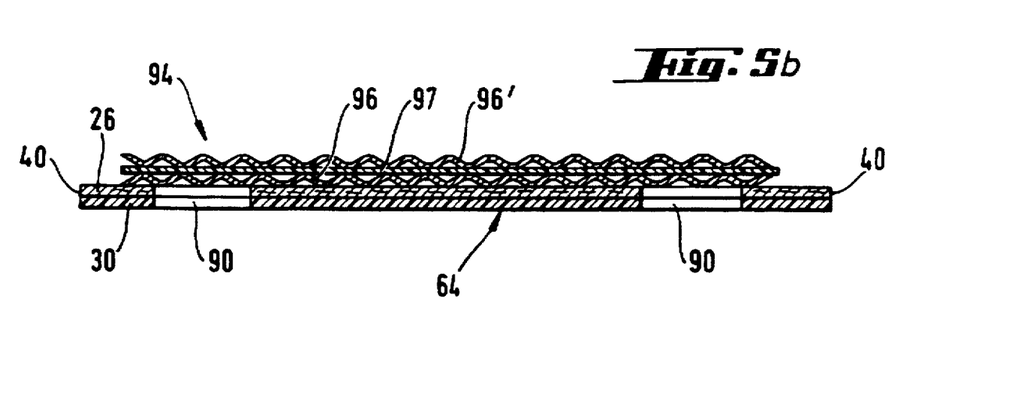

FIG. 5b depicts an embodiment wherein an elastic laminate 96,97,96' is located along the front waist edge 42' on the user-facing side of the topsheet 26. The elastic laminate in this case comprises two fibrous layers 96,96' which are connected to an elastomeric central layer 97 by means of adhesive or ultrasonic bonding.

The elastic elements 96,97 in the front waist region 42' exert a contractive force of between 20 and 250 g per inch of their width upon stretching by about 1 inch, preferably about 150 g.

Figure 6:
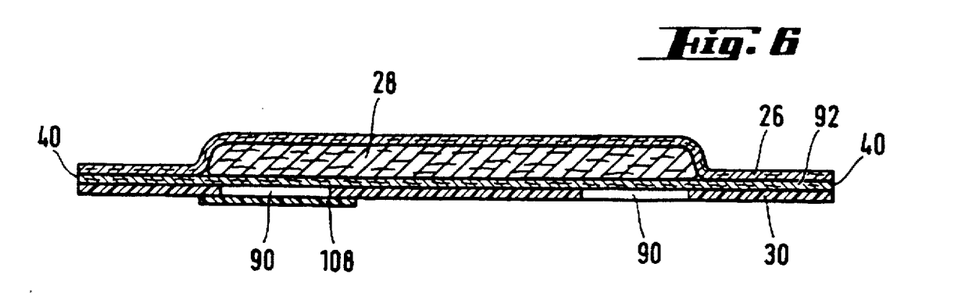
FIG. 6 shows a cross-sectional view of an absorbent article along a line of cross-section VI—VI of FIG. 1 located between the front and the back transverse edge and being substantially parallel thereto.

In the embodiment of FIG. 6, the cut-out regions 90 are located below the absorbent core 28. A tissue 92 is located below the core 28 and acts as a landing member 64. The tissue 92 further prevents the fibrous and, optionally, polymeric gelling material particles from migrating from the core 28 through the apertures 90. The cut out regions 90 in FIG. 6 may be located inside the front waist region 94 or outside the front waist region. The tissue 92 should be strong enough to withstand the shear forces exerted on it by the hook-type fastening members 58, which may be up to 50N for a fastening member of 30 mm×13 mm surface area. If the tissue 92 has insufficient tensile strength to withstand the shear forces exerted by the look-type fastening members 58, reinforcement fibers or reinforcement layers may be applied to the tissue.

The left hand cut-out section 90 in FIG. 6 is covered by a cover member 108, which may be formed by an adhesive tape. Removal of the tape 108, may be facilitated by providing a release coating around the cut-out section 90. Upon removal of the tape 108, the tissue 92 is exposed, as depicted for the right-hand cut-out section 90 in FIG. 6, and the fastening members 58 may be connected to the layer 92.

Figure 7:
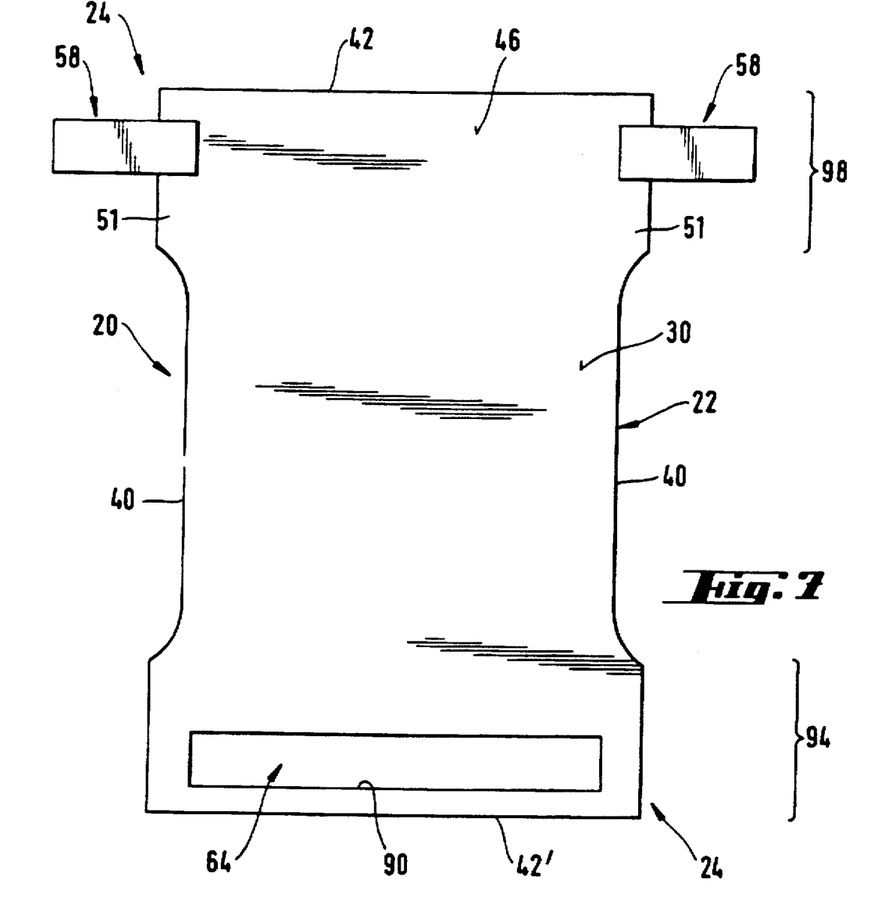
FIGS. 7–9 show plan views from the garment-facing side of the absorbent article of different embodiments of landing members.
Figure 8:
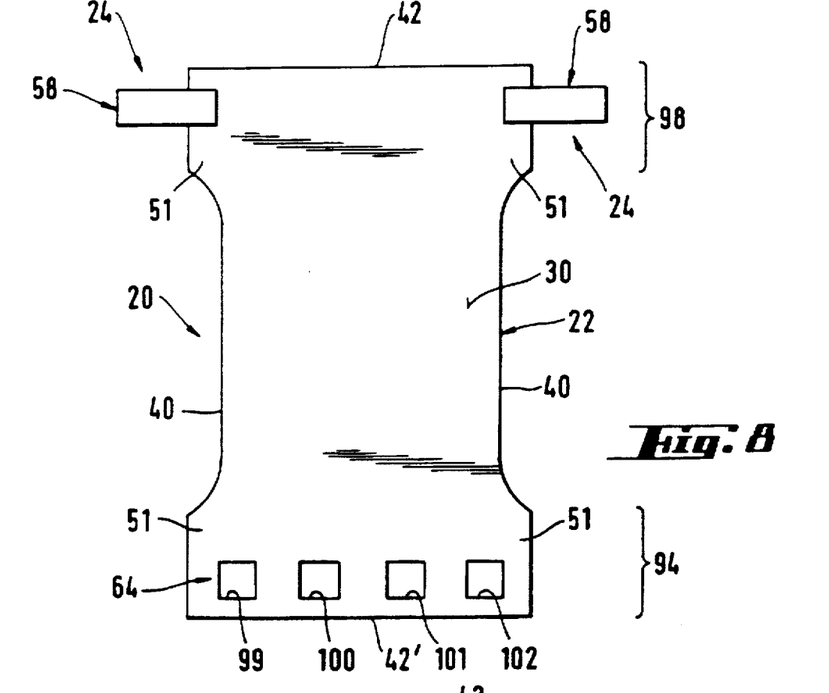

FIG. 7 schematically shows a plan view of the garment-facing side of an absorbent article 20 wherein the landing member 64 is comprised of a single stripshaped aperture in the backsheet 30 alongside the front transverse edge 42'. In the embodiment of FIG. 8, the landing member 64 comprises a number of individual cut out regions 99,100,101 and 102 located in the front waist region 94.

Figure 9:
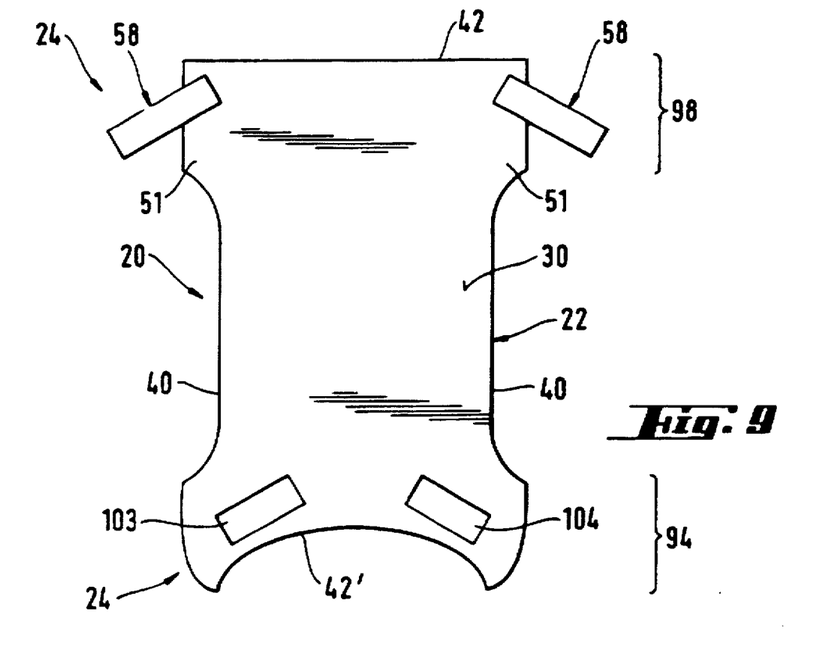

FIG. 9 shows an embodiment wherein the front transverse edge 42' is curved. The cut-out sections 103, 104 may be placed at an angle relative to the front transverse edge 42' to receive the angled fastening members 58. An absorbent article of this shape fits well below the belly of the wearer and will be located in the low-motion zone of the wearer. Hence the front waist region 94 will be subject to little movement and will stay properly in place.

Figure 10:
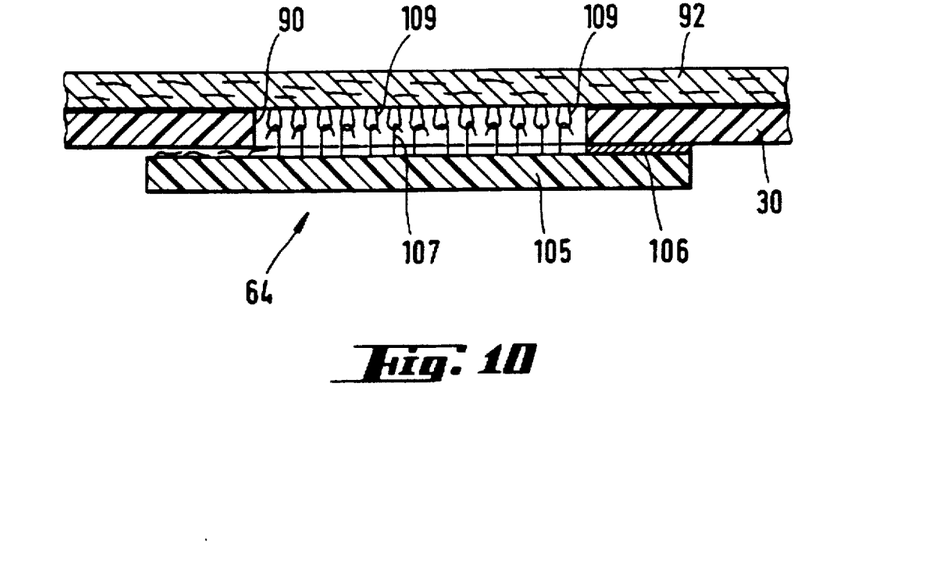
FIGS. 10 and 11 show a cross-sectional view of a cut-out section covered by cover member, FIGS. 12 and 13 respectively show a side elevational view of an absorbent article in the disposal configuration and of the position of the fastening members in the disposal configuration.
Figure 11:
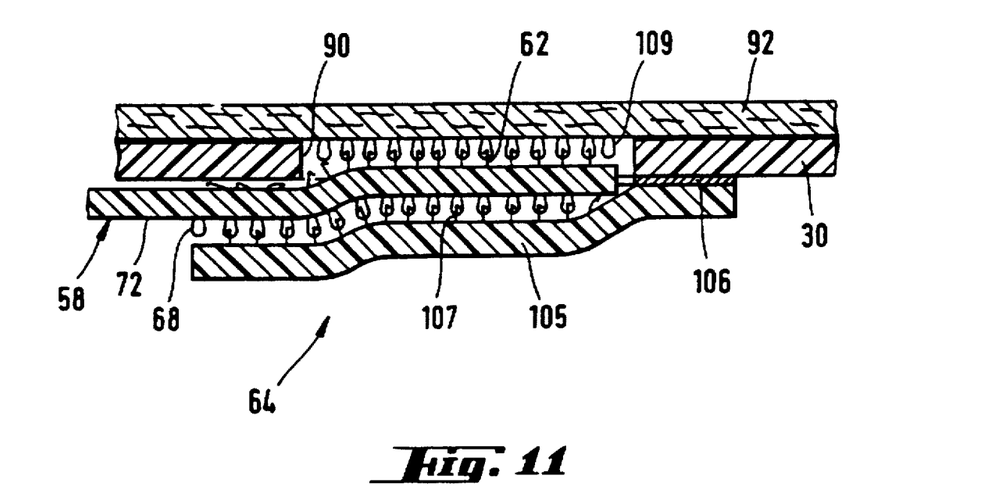

FIG. 10 shows a cross-sectional view through a landing member 64, wherein a cover member 105 overlies the cut-out section 90. The cover member 105 is at its side 106 permanently attached to the backsheet 30, for instance by means of adhesive bonding, an ultrasonic bond or pressure bonding. The hooks 107 of the cover member 105 engage the loops of the inner layer 92. When the diaper is put on a wearer, the cover member 105 is lifted, and the fastening member 58 is engaged with the inner layer 92, as shown in FIG. 11. The fastening member 58 comprises on its outwardly facing side 72 a loop-type material 68, which is also shown in FIG. 1. The cover member 105 can be connected to the loop-type material 68 of the fastening member 58 to provide a closure which has a large resistance against shear forces.

The configuration wherein the fastening members 58 comprise a loop-type material 68 on their backing surface 72 has as an additional advantage that the closure members 58 can be used to mutually engage for keeping the diaper 20 in a disposal configuration. This has been shown in FIGS. 12 and 13.

Figure 12:
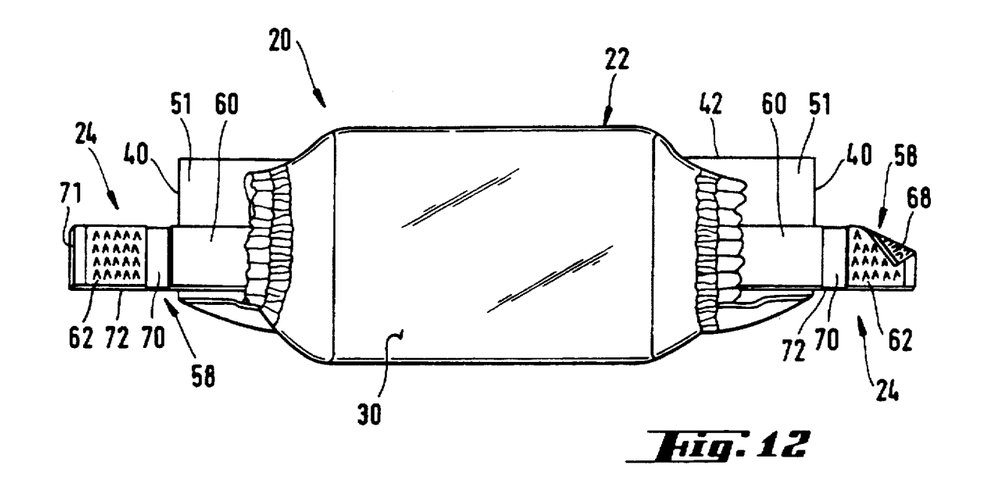
Figure 13:
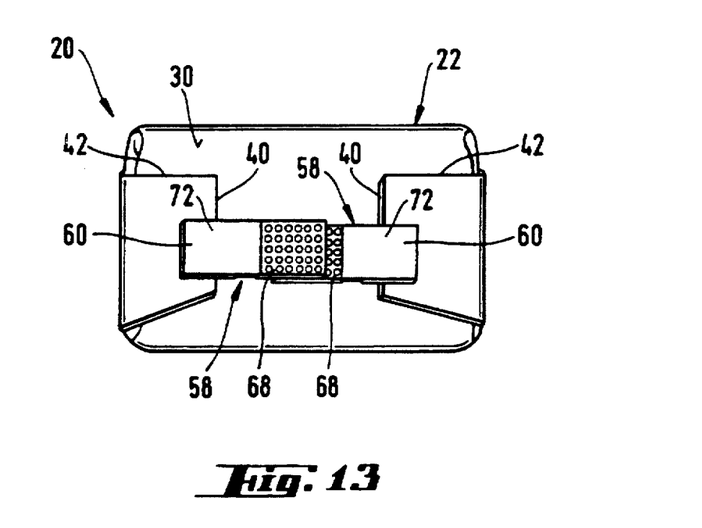

FIG. 12 shows the diaper 20 in a configuration wherein the diaper is rolled up from the front transverse edge 42' towards the back transverse edge 42. The backsheet 30 faces outwardly. The ears or panels 51 are folded around the rolled up diaper, and are mutually connected by engaging the hooks on the inner surface of one of the fastening members 58 with the loops on the outer surface of the other fastening member 58.

Figure 14:
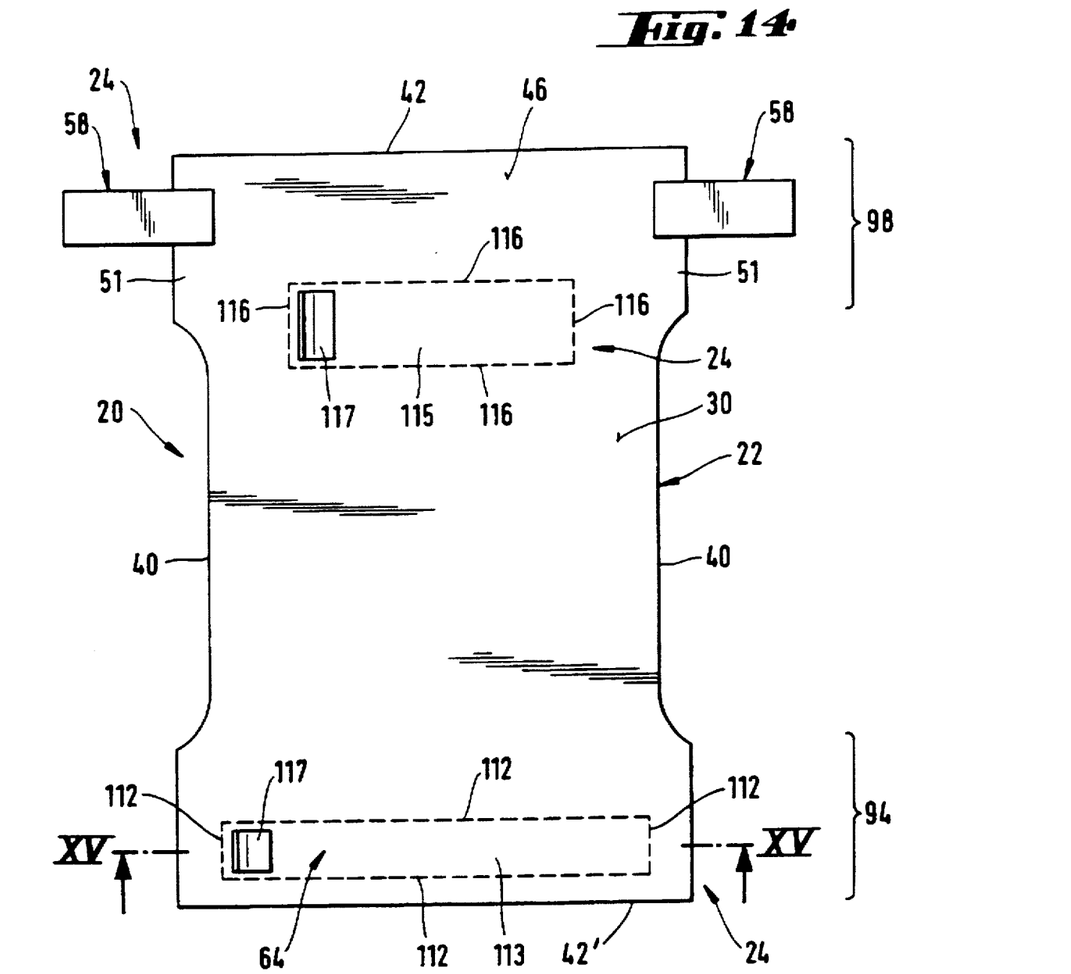
FIG. 14 shows a plan view of an absorbent article comprising a loop-type disposal member and a loop-type fastening member.
Figure 15:
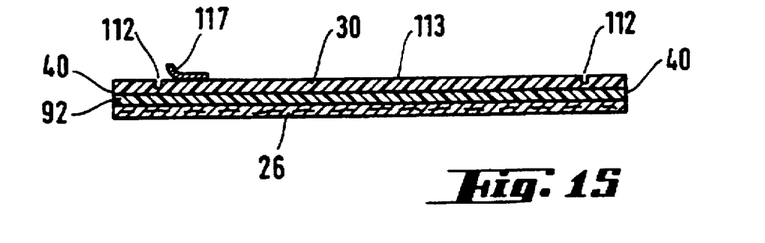

In FIG. 14, a top plan view of the garment-facing side of the diaper 20 is shown. In FIG. 14, the landing member 113 is covered by backsheet material which is provided with a line of weakening 112. The backsheet material can be manually removed from the landing member 113 by tearing the backsheet material along the line of weakening to expose the underlying layer 92. Tearing off the backsheet may be facilitated by a pull tab 117 attached to the backsheet in the region of the landing member 113. Especially in the embodiment wherein multiple separate landing zones 99, 100, 101, 102 are provided, as shown in FIG. 8, the selective removal of the backsheet material away from only those landing zones that are to be used, ensures that the liquid impervious properties of the backsheet 30 are maintained to a largest possible extent.

Figure 16:
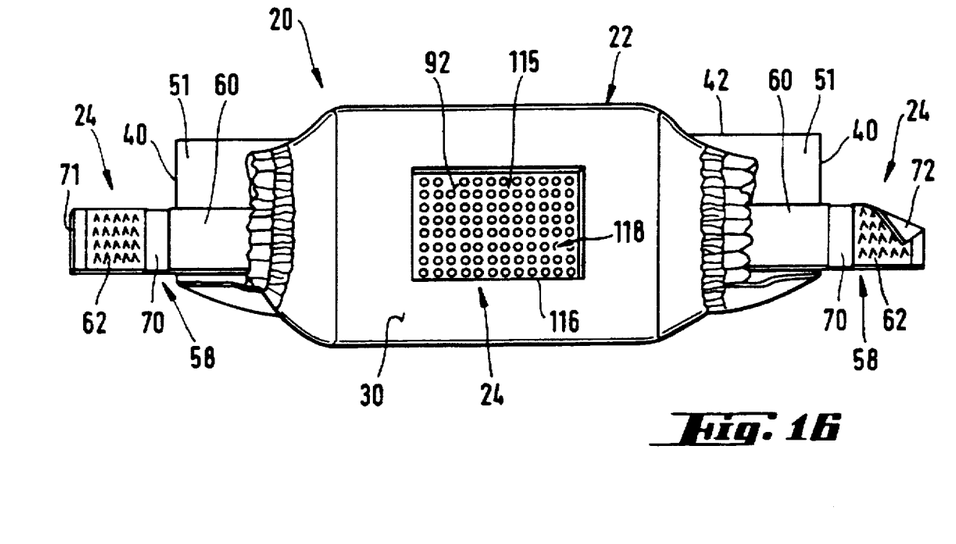
Figure 17:
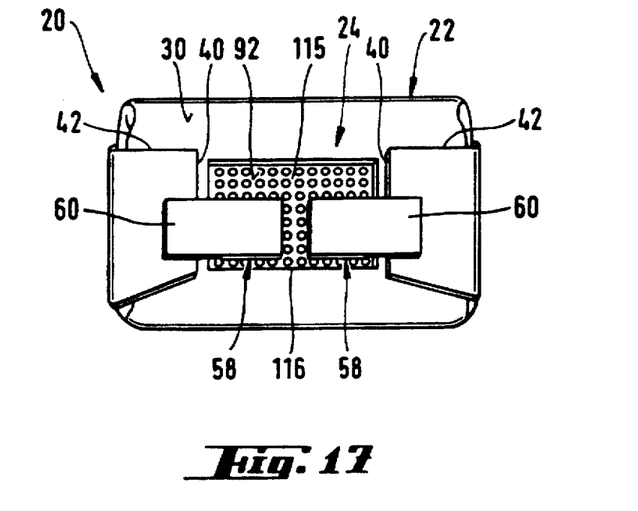

In FIG. 14 it is shown that a disposal member 115 is located on the backsheet 30 in the area of the back waist region 98. The disposal member 115 comprises a line of weakening 116 extending through the backsheet. The backsheet material can be removed from the disposal zone after use of the diaper 20. After placing the diaper into a disposal configuration as shown in FIG. 16, the hooks of the fastening members 58 can engage with the exposed material of the inner layer 92 through the cut out region 118 located inside the line of weakening 116. This has been depicted in FIG. 17. It should be noted that the disposal member 115 is not necessarily located adjacent the back transverse edge 42, but can be positioned anywhere between the landing member 113 and the back transverse edge 42. Again, a pull tab 117 may be connected to the backsheet material of disposal member 115.

It should be noted that in the embodiment of FIG. 14, either the landing members 113 or the disposal member 115 may be replaced by a separate patch of loop-type material that is attached to the garment-facing side of the backsheet.

I claim:

1. An absorbent article comprising:
   a backsheet having two longitudinal sides, a front transverse edge, a front waist region located along the the front transverse edge, a back transverse edge, and a back waist region located along the back transverse edge;
   a mechanical closing system comprising:
      at least two hook-type fastening members located in the back waist region and extending transversely beyond each longitudinal side, and
      a landing member for mechanically engaging with the hook-type fastening members; and
   an inner layer covering at least a part of the backsheet on a user-facing side thereof in the region of the landing member, wherein the landing member comprises at least one cut-out section extending through the backsheet and exposing the underlying inner layer, the inner layer being adapted to mechanically engage with the hook-type fastening members.

2. The absorbent article according to claim 1, wherein the landing member is located in the front waist region to form a fastening member for fixing the article on a wearer.

3. The absorbent article according to claim 2, wherein a further landing member is located between the front transverse edge and the back transverse edge to form a disposal member for keeping the article in a disposal configuration.

4. The absorbent article according to claim 1, wherein the landing member is located between the front transverse edge and the back transverse edge to form a disposal member for keeping the article in a disposal configuration.

5. The absorbent article according to claim 1, wherein the landing member comprises a plurality of individual cut-out sections in the backsheet.

6. The absorbent article according to claim 1, wherein the inner layer is formed by a liquid-pervious topsheet.

7. The absorbent article according to claim 1, wherein the inner layer is contracted by an elastic element located in the front waist region.

8. The absorbent article according to claim 1, wherein the inner layer is formed by a laminate of an elastomeric layer and a fibrous layer attached to said elastomeric layer, wherein the fibrous layer is located between the elastomeric layer and the backsheet.

9. The absorbent article according to claim 1, wherein the backsheet comprises a thermoplastic film or a laminate of a thermoplastic film and a fibrous material on the garment-facing side of the film, the inner layer comprising a nonwoven material.

10. The absorbent article according to claim 1, wherein the cut-out sections define a fit guide.

11. The absorbent article according claim 1, wherein the at least one cut-out section is covered by a detachable cover member.

12. The absorbent article according to claim 11, the cover member comprising a hook-type material, the cover member being permanently attached to the backsheet, the at least two hook-type fastening members comprising on their outer surface a loop-type fastening surface for engaging with the cover member.

13. The absorbent article according to claim 11, wherein for at least one cut out-section, the backsheet comprises a closed line of weakening, the cover member being formed by the backsheet material which can be removed to uncover the inner layer.

* * * * *